United States Patent [19]

Brooks et al.

[11] Patent Number: 5,352,662
[45] Date of Patent: Oct. 4, 1994

[54] INJECTABLE EXTENDED RELEASE FORMULATIONS AND METHODS

[76] Inventors: Norman D. Brooks, 5923 E. 300 N.; Gregory F. Needham, 1203 Sherwood Dr., both of Greenfield, Ind. 46140

[21] Appl. No.: 934,017

[22] Filed: Aug. 21, 1992

Related U.S. Application Data

[63] Continuation-in-part of Ser. No. 769,555, Oct. 1, 1991, abandoned.

[51] Int. Cl.$^5$ .................. A61K 37/36; A61K 37/18; A61K 9/10; A61K 37/00
[52] U.S. Cl. .................................. 514/12; 514/2; 514/21; 530/399
[58] Field of Search ............. 530/399; 514/2, 12, 514/21

[56] References Cited

U.S. PATENT DOCUMENTS

| | | | |
|---|---|---|---|
| 4,775,659 | 10/1988 | Thakkar et al. | 219/547 |
| 4,837,381 | 6/1989 | Steber et al. | 424/502 |
| 4,857,505 | 8/1989 | Arendl | 514/12 |
| 4,977,140 | 12/1990 | Ferguson et al. | 514/12 |
| 5,013,713 | 5/1991 | Mitchell | 514/2 |

FOREIGN PATENT DOCUMENTS

| | | |
|---|---|---|
| 0189673 | 8/1986 | European Pat. Off. |
| 0216485 | 1/1987 | European Pat. Off. |
| 0211691 | 2/1987 | European Pat. Off. |
| 0215313 | 3/1987 | European Pat. Off. |
| 0246540 | 5/1987 | European Pat. Off. |
| 0257368 | 3/1988 | European Pat. Off. |
| 0278103 | 8/1988 | European Pat. Off. |
| 0314421 | 10/1988 | European Pat. Off. |
| 0368247 | 7/1989 | European Pat. Off. |
| 58172311 | 10/1983 | Japan . |
| 2167622 | 11/1985 | United Kingdom . |
| WO88/00059 | 1/1988 | World Int. Prop. O. |

OTHER PUBLICATIONS

Hawley's Condensed Chemical Dictionary, 11th Ed., p. 567.
"Monograph French Pharmacopeia" 10th Edition, 1990, entries on Polyglycolized Glycerides and Saturated Polyglycolized Glycerides, including translations by Gattefossé Corporation.
Brown et al., "Chemical Synthesis and Cloning of a Tyrosine tRNA Gene", *Methods in Enzymology,* vol. 68, pp. 109–151 (1979).
Baichwal, M. R. et al., "Sustained Release Capsules Using Polyglycerol Esters", *The Indian Journal of Pharmacy,* vol. 35, No. 4, pp. 146–150 (1973).
Labhasetwar, P. K. et al., "Study of Shellac Glycerol Esters as Microencapsulating Materials", *J. Microencapsulation,* vol. 6, No. 1, pp. 115–118 (1989).
Starha, L., et al., "Higher Fatty Acids and Their Glycerol Esters in per os Administered Medicines with Protracted Action", Acta Facultatis Pharmaceuticae Universitatis Comenianea, vol. 21, pp. 193–194 (1972).
Babayan, V. K., "Polyfunctional Polyglycerols and Their Esters", *Food Product Development,* Apr.–May (1968).

*Primary Examiner*—Howard E. Schain
*Assistant Examiner*—Phynn Touzeau

[57] ABSTRACT

Described is a preferred injectable, extended release formulation which includes a growth hormone or a growth hormone releasing factor in a carrier including a biocompatible hydrophobic vehicle and an amount of polyglycerol ester effective to extend release of the growth hormone or growth hormone releasing factor in an animal. Other preferred embodiments provide methods for making a composition for treating an animal with a growth hormone or growth hormone releasing factor, and methods for administering these substances to an animal.

60 Claims, 6 Drawing Sheets

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 75 Amino Acids
( B ) TYPE: Amino Acids
( C ) STRANDEDNESS: Single
( D ) TOPOLOGY: Linear ( i i ) MOLECULE TYPE: Peptide ( x i ) SEQUENCE DESCRIPTION: SEQ ID NO:1:

| Ala | Asp | Ala | Ile | Phe | Thr | Asn | Asn | Tyr | Arg | Arg | Val | Leu | Thr | Gln |
|-----|-----|-----|-----|-----|-----|-----|-----|-----|-----|-----|-----|-----|-----|-----|
| 1   |     |     |     | 5   |     |     |     |     | 10  |     |     |     |     | 15  |
| Leu | Ser | Ala | Arg | Arg | Leu | Leu | Gln | Asp | Ile | Leu | Ser | Arg | Gln | Gln |
| 20  |     |     |     |     | 25  |     |     |     |     | 30  |     |     |     |     |
| Gly | Glu | Arg | Asn | Gln | Glu | Gln | Gly | Ala | Arg | Val | Arg | Leu | Gly | Arg |
| 35  |     |     |     |     | 40  |     |     |     |     | 45  |     |     |     |     |

-continued

```
Gln  Val  Asp  Ser  Leu  Trp  Ala  Asp  Gln  Arg  Gln  Leu  Ala  Leu  Glu
 50                  55                       60

Ser  Ile  Leu  Ala  Thr  Leu  Leu  Gln  Glu  His  Arg  Asn  Ser  Gln  Gly
 65                  70                       75
```

( 2 ) INFORMATION FOR SEQ ID NO: 2:

( i ) SEQUENCE CHARACTERISTICS:
        ( A ) LENGTH: 234 Base Pairs
        ( B ) TYPE: Nucleic Acid
        ( C ) STRANDEDNESS: Single
        ( D ) TOPOLOGY: Linear     ( i i ) MOLECULE TYPE: DNA (genomic)

( x i ) SEQUENCE DESCRIPTION: SEQ ID NO:2:

```
ATG  GCT  GAT  GCT  ATT  TTT  ACT  AAT  AAT  TAT  CGA  CGC  GTT  CTT  ACT  CAG    48

CTG  TCT  GCT  CGT  CGT  CTG  CTG  CAG  GAT  ATT  CTG  TCT  CGT  CAG  CAG  GGT    96

GAA  CGT  AAC  CAG  GAA  CAA  GGA  GCT  CGT  GTT  CGT  CTT  GGT  CGT  CAG  GTT   144

GAT  TCT  CTG  TGG  GCT  GAT  CAA  CGT  CAG  CTT  GCT  CTC  GAG  TCT  ATC  CTG   192

GCT  ACT  CTG  CTG  CAG  GAA  CAT  CGT  AAT  TCT  CAG  GGT  TAA  TAG            234
```

INJECTABLE EXTENDED RELEASE FORMULATIONS AND METHODS

REFERENCE TO RELATED APPLICATION

This is a continuation-in-part of pending U.S. patent application Ser. No. 07/769,555, filed Oct. 1, 1991, now abandoned.

BACKGROUND

This invention relates generally to the administration of bioactive substances to animals. More particularly, this invention relates to injectable compositions and methods for extended release of macromolecules such as growth hormones and growth hormone releasing factors in animals.

In recent years, major efforts have been made to discover cost-efficient ways to treat animals with growth hormones, growth hormone releasing factors and other bioactive substances over extended periods of time. The achievement of effective extended release (also commonly referred to as "sustained" or "prolonged" or "controlled" release) compositions and methods has been central in these efforts. These compositions and methods are designed to deliver effective amounts of bioactive substance over extended periods of time following administration. This reduces labor costs by reducing the number of administration procedures during an overall treatment regimen. Extended release of the substance also allows for treatment in situations where it would otherwise be impracticable, for instance during range feeding of animals raised for consumption. Further, effective extended release avoids large fluctuations in plasma levels of the bioactive substance, initially too high and then rapidly too low, which occur upon injection of standard, non-extended release formulations.

There has remained a need for improved injectable compositions and methods which provide extended release of growth hormone-related substances such as growth hormones and growth hormone releasing factors in animals. The compositions preferably are easily formulated using readily available materials, and the preferred preparative procedures should not be potentially damaging to the active materials.

SUMMARY OF THE INVENTION

The present invention addresses these and other needs and in one preferred embodiment provides a composition of matter comprising an injectable extended release formulation including a growth hormone-related substance selected from the group consisting of growth hormones and growth hormone releasing factors in a carrier including a biocompatible hydrophobic vehicle, e.g. an oil, and an effective amount of polyglycerol ester to extend release of the substance in an animal.

Another preferred embodiment provides a method for making a composition for treating an animal with a growth hormone or growth hormone releasing factor. The method includes incorporating the growth hormone or growth hormone releasing factor in a carrier including polyglycerol ester and a biocompatible hydrophobic vehicle, to thereby form an injectable extended release formulation. In a preferred mode, polyglycerol ester and a biocompatible hydrophobic vehicle are mixed at an elevated temperature to form the carrier, the carrier is cooled, and the growth hormone or growth hormone releasing factor is then dispersed in the carrier. The polyglycerol ester is included in an effective amount to extend release of the growth hormone or growth hormone releasing factor in an animal.

Still another preferred embodiment of the invention provides a method for administering a growth hormone or growth hormone releasing factor to an animal. This method comprises the step of injecting into the animal an injectable, extended release formulation including a growth hormone-related substance selected from the group consisting of growth hormones and growth hormone releasing factors in a carrier including a biocompatible hydrophobic vehicle and an effective amount of polyglycerol ester to extend release of the substance in the animal.

The invention thus provides extended release compositions which are highly effective and readily prepared. Further, this efficacy can be achieved in an injectable paste composition which does not require forcible compression of the growth hormone or growth hormone releasing factor with other materials to form solid implants. Further, treatments of the invention can be performed without incision, which for example is required with solid extended release implants. Moreover, these advantages can be achieved while providing effective extended release of growth hormone for up to and exceeding one month after administration, and providing extended release of growth hormone releasing factor so as to cause elevated growth hormone levels for up to and exceeding two weeks after administration. Additional embodiments, aspects and advantages of the invention will be apparent from the following description and appended claims.

DETAILED DESCRIPTION OF THE INVENTION

For the purpose of promoting an understanding of the principles of the invention, reference will now be made to certain embodiments and specific language will be used to describe the same. It will nevertheless be understood that no limitation of the scope of the invention is thereby intended, such alterations, further modifications and applications of the principles of the invention as described herein being contemplated as would normally occur to one skilled in the art to which the invention relates.

As indicated above, a preferred embodiment of the invention provides, as a composition of matter, an injectable extended release formulation which includes a growth hormone or a growth hormone releasing factor in a carrier containing a biocompatible hydrophobic vehicle such as an oil and an effective amount of polyglycerol ester to extend release of the hormone or growth hormone releasing factor in an animal. This formulation provides delivery of an efficacious dose of the hormone or releasing factor to the animal over prolonged periods of time following injection. The animal can be any species which produces endogenous growth hormones, including vertebrate species such as cattle, sheep, swine, goats, horses, birds, fish and humans.

The present invention is based on the discovery that effective extended release of growth hormone and of growth hormone releasing factor (hereinafter "GRF", also commonly known as growth releasing factor, growth hormone releasing hormone, growth releasing hormone, and somatocrinin) can be achieved with an injectable formulation in which the active material, i.e. growth hormone or GRF, is in a carrier including polyglycerol ester and an oil or similar vehicle. In a preferred aspect, the growth hormone or GRF is in simple admixture with the carrier, and thus need not be incorporated into particles by a hot melt procedure or the like. Thus, as used herein, the term "in simple admixture" is intended to describe a condition in which the growth hormone or GRF is not incorporated into the polyglycerol ester by mixing the growth hormone or GRF with melted ester which is thereafter solidified. Instead, preferred formulations of the invention include the bioactive substance in simple admixture with a carrier including a hydrophobic vehicle and polyglycerol ester, wherein the overall formulation is an injectable paste providing extended release of the substance. As a result, the formulations of the invention are readily prepared.

The growth hormone or GRF to be utilized in the present invention can be any substance, of natural or synthetic origin, which exhibits the biological properties of a natural growth hormone or natural GRF. The natural growth hormone or GRF can be of any species, such as bovine, ovine, caprine, equine, porcine, avian, fish, human, and the like. Natural growth hormones or GRFs are extracted from the appropriate glandular tissue of animals; procedures for accomplishing this are known, albeit tedious. However, it is now well established practice to synthesize growth hormones, GRFs and other such substances by the use of genetically modified microorganisms. It is oftentimes convenient or even preferred that such processes yield a modified growth hormone or GRF, that is, a substance that differs as to its structure from the naturally occurring growth hormone or GRF, but which retains the biological activity of the naturally occurring growth hormone or GRF. For example, a modified growth hormone or GRF may contain one or more additional amino acids, at one or both ends of the polypeptide chain; may have an amino acid sequence which differs from that of naturally occurring growth hormone or GRF; or may be an active fragment of naturally-occurring growth hormone or growth hormone releasing factor. For example, in the case of GRF, naturally occurring GRFs, pre-proteins of naturally occurring GRFs and fragments of naturally occurring GRFs (e.g. 29 amino acid growth hormone releasing factor) are known to cause elevation of growth hormone levels. Additional modifications will be understood by those skilled in the art. Therefore, the teems "growth hormone" and "growth hormone releasing factor" (or "GRF" ) are used throughout this document to refer to both naturally occurring growth hormones and GRFs as well as synthetically produced substances which share the biological properties of naturally occurring growth hormones or GRFs, and which may be identical or which may vary as to structure.

The present invention is especially preferred for use with bovine growth hormones including a synthetically produced modification of bovine growth hormone. Two examples of synthetically produced bovine growth hormone are the compounds known as somidobove and sometribove.

The present invention is also preferred for use with porcine and bovine growth hormone releasing factors and synthetically produced modifications of these factors. A particularly preferred example is the growth hormone releasing factor identified in Example 23, below.

As will be understood, the growth hormone or GRF can be provided in various physical forms. For instance, it can be a powder, e.g. air milled to decrease particle size, granules, etc. To date, air milled powder-form bovine growth hormone as taught by EPO 0384752, published Aug. 29 , 1990, has been preferred.

The term "polyglycerol ester" is used herein in accordance with the art. Thus, "glycerol" refers to the simple compound HO—$CH_2$—CH(OH)—$CH_2$—OH. Polyglycerol refers to the polymeric versions of glycerol. Thus, "polyglycerol" in the present invention means a compound having the formula HO—[$CH_2$—CH(OH)—$CH_2$—O]$_n$H, with n=at least 2 and generally not more than 12 . Polyglycerol includes for example diglycerol, triglycerol, tetraglycerol, pentaglycerol, hexaglycerol, heptaglycerol, nonaglycerol, and decaglycerol . "Polyglycerol ester" further means that there is at least partial esterification, that is, one or more of the OH radicals has been esterified. The maximum number of esterification sites in a particular polyglycerol is determined by the formula n+2 . For the purposes of the present invention, the identity of the ester is not critical. In general, the esterification is by a fatty acid having from about 4 to 30 carbon atoms and generally from about 12 to about 22 carbon atoms, including the carboxylic acid carbon atom in the count. Suitable ester groups include the following: laurate, myristate, palmirate, stearate, arachidate, behenate, lignocerate, palmitoleate, oleate, linoleate, linolenate, arachidonate, and the like.

Further useful information concerning glycerol and polyglycerol esters is found in an article by V. K. Babayan, "Polyfunctional Polyglycerols and Their Esters", in Food Product Development, April-May, 1968, which is herein incorporated by reference.

It is not required that the polyglycerol be uniformly of one substance: mixtures are suitable. Similarly, it is not required that the esterification be uniformly by one acid; a polyglycerol ester containing a mixture of ester groups is fully usable.

However, certain preferences have been discovered. One preference is for a completely esterified polyglycerol, that is, one in which n+2 ester groups are present. Also, while the polyglycerols include members which are variously liquid or semi-solid (i.e. "paste"), it has been found that those which are semi-solid are preferred. Based on these preferences, the following are regarded as preferred substances for use in the present invention:

diglycerol tetraesters, generally
diglycerol tetrastearate
triglycerol pentaesters, generally
tetraglycerol hexaesters, generally
pentaglycerol heptaesters, generally
hexaglycerol octaesters, generally
decaglycerol dodecaesters, generally Other preferred polyglycerol esters will be readily apparent.

Polyglycerol ester is included in an amount sufficient to provide extended payout of the growth hormone or GRF in the animal treated. For example, preferred formulations of growth hormone will provide increased levels of the growth hormone in the animal for at least 14 days after injection, more preferably at least 21 days, and highly preferably for at least about 28 days after injection. Preferred formulations of GRF will provide increased levels of growth hormone in the animal at least 7 days after injection, more preferably at-least about 14 days. Typically, preferred formulations of the invention will include a carrier comprised about 5% by weight to about 60% by weight of polyglycerol ester, depending on such factors as the particular vehicle, growth hormone or GRF, and other ingredients to be included, as well as the desired functional, physical and other-characteristics of the final formulation. More preferred formulations include carriers comprised about 20% by weight to about 60% by weight of polyglycerol ester.

As will be appreciated, any biocompatible oil or other hydrophobic vehicle will be suitable for the invention. Representative oils are mineral and various other oils, which are liquid at room temperature, including, but not limited to, peanut oil, sesame seed oil and soybean oil. The hydrophobic vehicle is included in an amount sufficient to provide the desired viscosity of the total formulation, which will of course vary according to the circumstances. Typically, the carrier will be comprised about 40% by weight to about 95% by weight of the vehicle, and in more preferred formulations about 40% by weight to about 80% by weight. Sesame seed oil has been preferred from work thus far.

As to the relative amounts of polyglycerol ester and vehicle, preferred formulations have a weight ratio of polyglycerol to oil of about 10:90 to about 60:40.

The injectable formulation will include an effective amount of growth hormone or GRF. Determining this amount is within the skill of the ordinary artisan. In the preferred case of bovine growth hormone, it is included in an amount of about 5% to about 50% by weight of the formulation, preferably about 10% to 25% by weight. In the case of GRF, it is preferably included in an amount in the range of about 10% to about 40% by weight of the formulation.

In addition to the oil and polyglycerol ester, various known adjuvants or excipients may be present in the carrier. These include for example beeswax, aluminum monostearate, carnauba, paraffin and the like. Dissolution enhancers such as sucrose and polyethylene glycol, dyes, preservatives, antibiotics, antioxidants, stabilizers and other conventional ingredients may also be included. When present, these additional ingredients usually comprise about 0.01% by weight to about 10% by weight of the carrier.

Another feature of the invention relates to the surprising discovery that polysaccharides such as dextran can be included in the carrier to dramatically extend payout of growth hormone and GRF as illustrated in the Examples below and accompanying Figures. Thus, injectable extended release formulations having growth hormone or GRF, and a carrier including hydrophobic vehicle, polyglycerol ester and sufficient dextran to further extend release provide another important aspect of the invention. In these preferred formulations, sufficient dextran is included to provide the desired growth hormone or GRF extended release profile while maintaining the overall formulation suitable for administration through a syringe. Typically, dextran will be included in the range of about 1% to about 10% by weight relative to the polyglycerol ester and hydrophobic vehicle present, with at least about 8% by weight proving highly effective in work thus far with growth hormone as illustrated in Example 10 below and at least about 5% proving highly effective in work thus far with GRF as illustrated in Examples 14–16 and 20–22 below.

Generally, formulations of the invention can be prepared by heating and mixing the polyglycerol ester in the hydrophobic vehicle to formulate the carrier. The carrier is then cooled, for instance to about 40°–45° C. or less, and conveniently to ambient temperature (e.g. about 25° C.), and the growth hormone or GRF is blended with the carrier at the desired level. When included, dextran can also be mixed in the vehicle prior to cooling and adding the growth hormone or GRF.

The preferred overall formulations of the invention are syringeable, for example through a 14 gauge needle, and can be administered by injection into the subcutaneous space.

To promote a further understanding of the principles and advantages of the invention, the following examples are provided. It will be understood, however, that these examples are illustrative, and not limiting, of the invention.

EXAMPLES 1–3

Preparation of Formulations of Growth Hormone

A carrier was prepared by combining 2952 milligrams (mg) diglycerol tetrastearate with 4428 mg of sesame seed oil (providing a 40:60 weight ratio of polyglycerol ester to oil vehicle) and warming the resulting mixture on a hot plate to melt and mix the components. The carrier was then cooled to room temperature (approx. 25° C.) on a wrist shaker. After the carrier was cooled, 1620 mg of somidobove (air milled, 81.5% potency) were added and mixed in with a spatula at room temperature. The resulting inventive formulation (EX1), containing 14.67% of somidobove, was placed into a 10 cc syringe from which it was syringed into four 6 cc syringes to 1.91 grams±5%.

Two more inventive formulations were prepared as described, except using weight ratios (diglycerol tetrastearate: sesame oil) of 35:65 and 20:80, respectively. The resulting paste formulations are designated EX2 and EX3, respectively.

Administration and Testing

Figure 1:
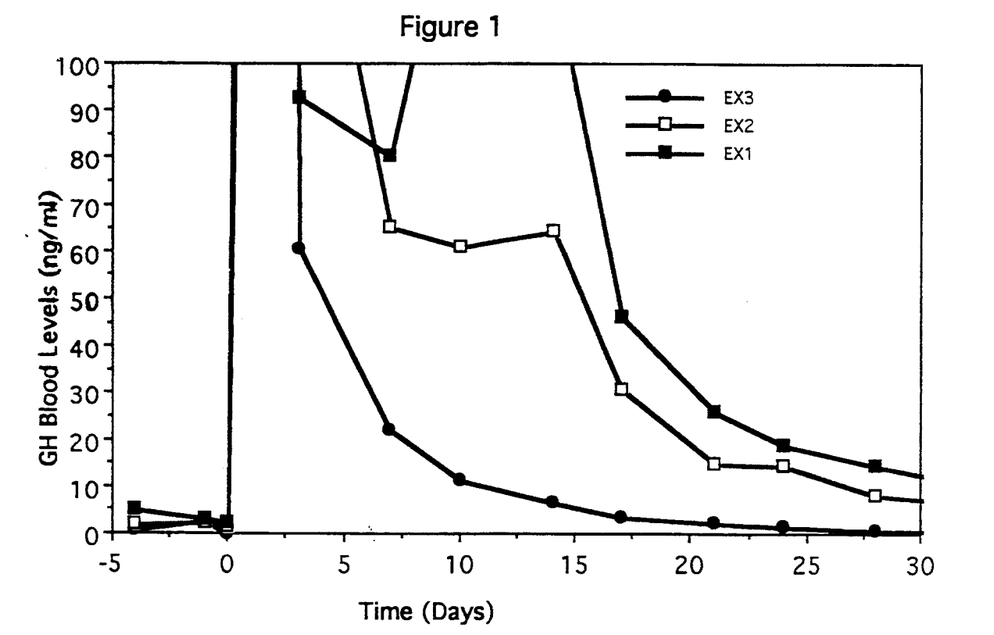
FIGS. 1 and 2 are graphs showing post-injection plasma bovine growth hormone levels (nanogram per milliliter of plasma (ng/ml.)) over time (days) for growth hormone formulations of the invention.

Plasma specimens were taken from sheep subjects and individually tested to determine pre-treatment plasma growth hormone levels. Each of the formulations EX1, EX2 and EX3 was then injected subcutaneously into a respective sheep subject, and the plasma bovine growth hormone levels monitored every few days over a 32 day cycle. The results are set forth in FIG. 1, which is a graph of plasma growth hormone levels over time for the respective subjects. As illustrated, the EX1, EX2 and EX3 formulations provide highly advantageous extended release profiles.

EXAMPLE 4

Another growth hormone formulation was prepared as follows. A carrier was prepared by combining 6642 mg of sesame seed oil with 738 mg hexaglycerol distearate and warming the resulting mixture on a hot plate to melt and mix the components. The carrier was then cooled to room temperature (approx. 25° C.) on a wrist shaker. After the carrier was cooled, 1620 mg of somidobove (air milled, 81.5% potency) were added and mixed in with a spatula at room temperature. The resulting formulation (EX4) was placed into a 10 cc syringe from which it was syringed into four 6 cc syringes to 1.91 grams ±5%. In testing analogous to that described in Examples 1-3, advantageous extended release characteristics were also obtained with the EX4 formulation.

EXAMPLES 5-9

Several additional growth hormone formulations were prepared according to the invention as summarized in Table 1 below. The indicated vehicle was combined with the polyglycerol ester in the ratios shown (10000 milligrams total) and warmed on a hot plate to melt and mix. The mixture was then placed on a wrist action shaker until it cooled to room temperature. Somidobove was then formulated at 14.67% by weight into each carrier and mixed with a spatula at room temperature. The resulting light paste formulations were then loaded into 5 cc syringes and placed in a freezer overnight. The formulations were tested the next day for syringeability through a 14 gauge needle and the results are given in Table 1.

TABLE 1

| EX | Polyglycerol Ester | Vehicle | Ratio[a] | Results |
|----|-------------------|---------|-------|---------|
| 5 | Diglycerol Tetrastearate | Decaglycerol Decaoleate | 30/70 | syringeable |
| 6 | Hexaglycerol Distearate | Sesame oil | 5/95 | syringeable |
| 7 | Decaglycerol Decastearate | Sesame oil | 30/70 | syringeable |
| 8 | Hexaglycerol Distearate | Decaglycerol Decaoleate | 20/80 | syringeable |

[a]weight ratio of Polyglycerol Ester to Vehicle.

EXAMPLES 9-10

Figure 2:
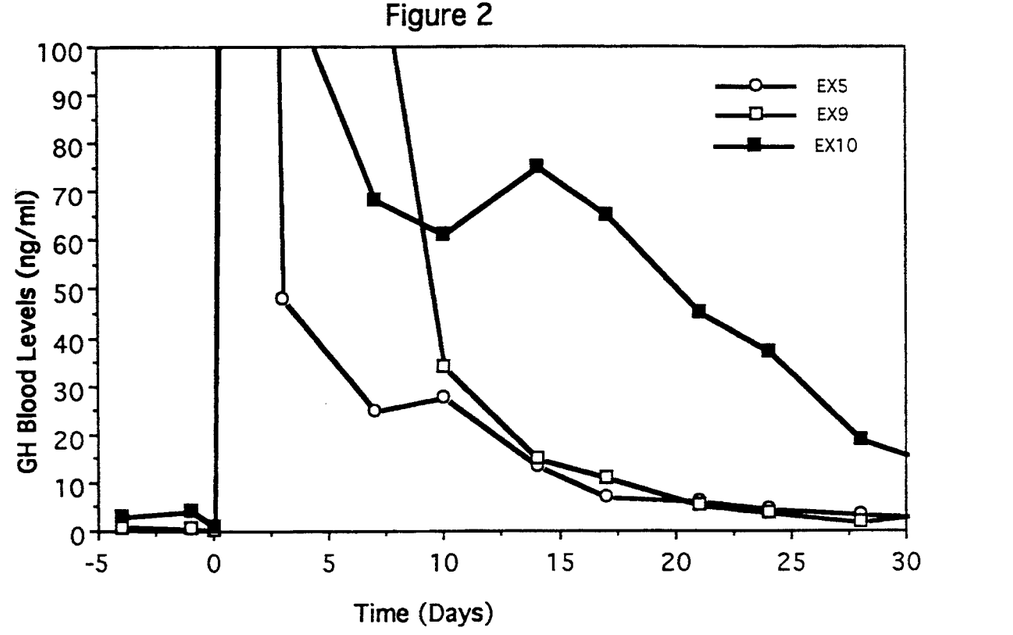
Figure 3:
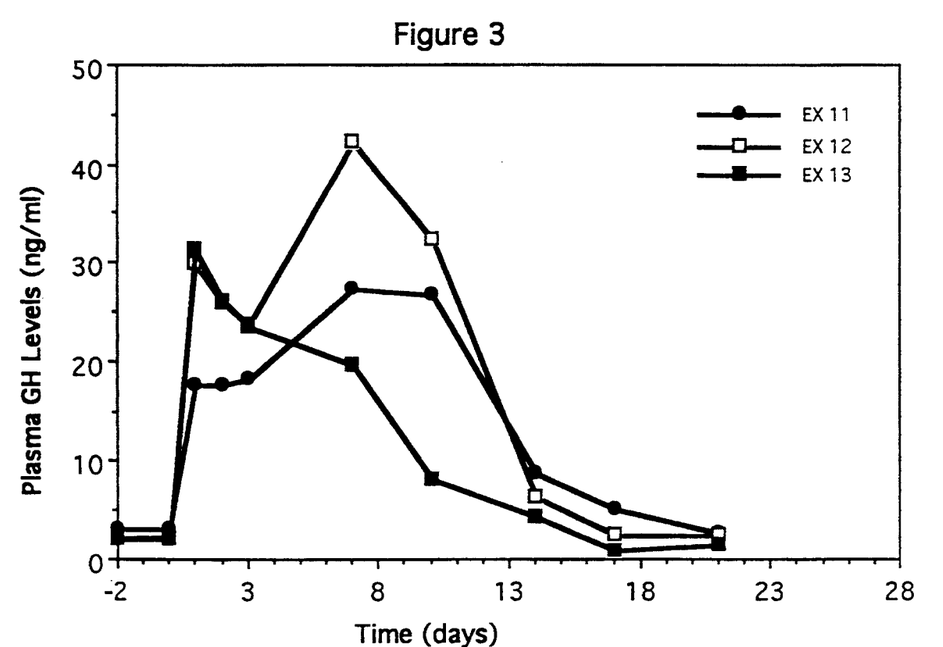
FIGS. 3–6 are graphs showing post-injection plasma growth hormone levels (ng/ml) over time (days) for growth hormone releasing factor formulations of the invention.
Figure 4:
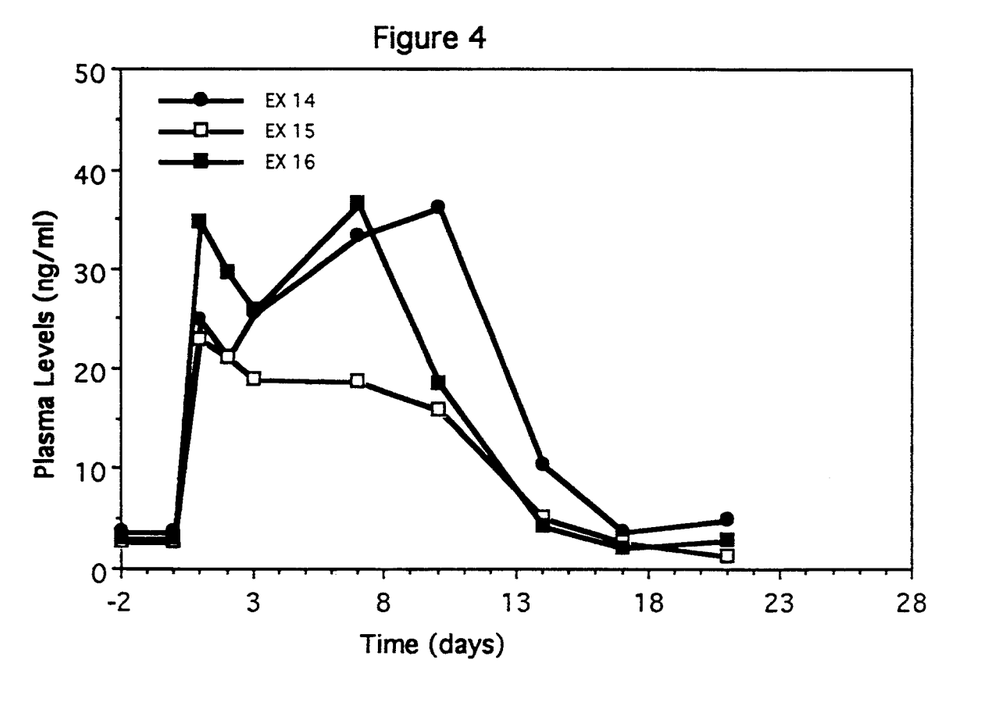
Figure 5:
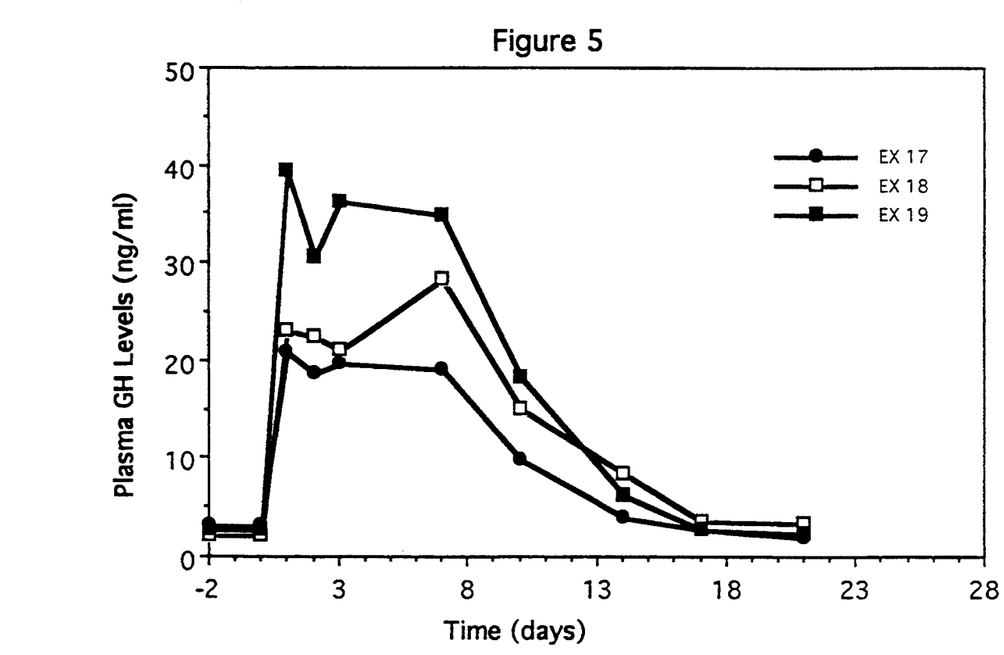
Figure 6:
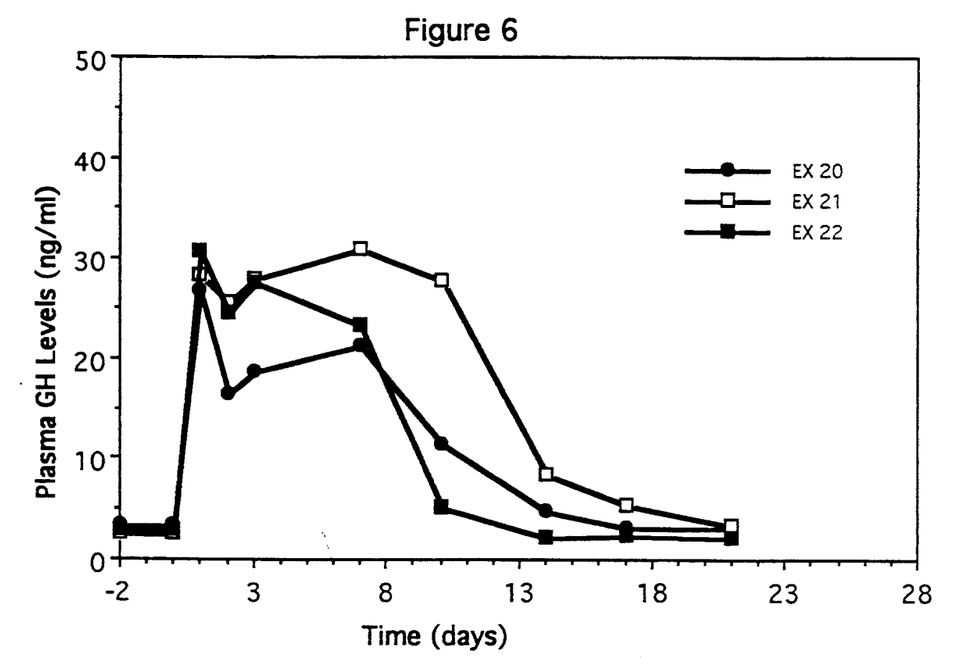

In a set of experiments it was demonstrated that polysaccharides such as dextran can be added to polyglycerol ester-containing formulations to extend duration of release of bovine growth hormone. Accordingly, 2480 mg diglycerol tetrastearate and 295 mg dextran (molecular weight 150,000) were combined with 4605 mg sesame seed oil (to provide a 33.6:62.4:4.0 weight ratio of polyglycerol ester:oil:dextran) and warmed to mix. The mixture was then cooled to room temperature with stirring, after which 1620 mg somidobove (air milled, 81.5% potency) were blended into the carrier with a spatula to achieve a formulation (EX9) having 14.67% by weight somidobove loading. Another dextran-including paste formulation (EX10) was prepared in this same manner, except the carrier was made up having a polyglycerol ester:dextran:oil weight ratio of 30:8:62. These two formulations were tested alongside EX5. The results of this testing are set forth in FIG. 2. As can be seen, dextran can be added in amounts sufficient to achieve significant extension of release. Looking at EX10, extended release can be seen even over and above EX1 (see Example 1 and FIG. 1).

EXAMPLES 11-22

Preparation of GRF Formulations

A number of formulations of the GRF analog described in Example 23 were prepared according to the invention as summarized in Table 2 below. The indicated vehicle was combined with the polyglycerol ester in the weight ratios shown (2800 mg total) and warmed on a hot plate to melt and mix (at 70° C.). The mixture was then removed from the hot plate and allowed to cool at room temperature, and then the GRF was added to 20% by weight of the formulation just as the polyglycerol ester began to solidify and stirred in the carrier with a spatula. The mixture was then allowed to cool at room temperature and mixed again. The resulting light paste formulations were refrigerated for two days and then warmed to room temperature. Subsequently, the formulations were stirred again and loaded into 3 cc syringes. The formulations were then loaded from the 3 cc syringes into 1 cc syringes at a level of 0.30 g±0.01 g each.

TABLE 2

| EX | Polyglycerol Ester | Vehicle | Other | Ratio[a] |
|----|-------------------|---------|-------|-------|
| 11 | Diglycerol Tetrastearate | Sesame Oil | — | 40/60 |
| 12 | Diglycerol Tetrastearate | Sesame Oil | — | 30/70 |
| 13 | Diglycerol Tetrastearate | Sesame Oil | — | 10/90 |
| 14 | Diglycerol Tetrastearate | Sesame Oil | Dextran | 37.5/57.5/5 |
| 15 | Diglycerol Tetrastearate | Sesame Oil | Dextran | 27.5/67.5/5 |
| 16 | Diglycerol Tetrastearate | Sesame Oil | Dextran | 7.5/87.5/5 |
| 17 | Hexaglycerol Distearate | Sesame Oil | — | 40/60 |
| 18 | Hexaglycerol Distearate | Sesame Oil | — | 30/70 |
| 19 | Hexaglycerol Distearate | Sesame Oil | — | 10/90 |
| 20 | Hexaglycerol Distearate | Sesame Oil | Dextran | 37.5/57.5/5 |
| 21 | Hexaglyerol Distearate | Sesame Oil | Dextran | 27.5/67.5/5 |
| 22 | Hexaglycerol Distearate | Sesame Oil | Dextran | 7.5/87.5/5 |

[a]Weight ratio of Polyglycerol Ester to Vehicle, or, where Dextran is included, of Polyglycerol Ester to Vehicle to Dextran Administration and Testing

Pretreatment plasma growth hormone levels were taken from 72 sheep each weighing approximately 60 kg. The formulations EX 11 through EX 22 were then injected subcutaneously each into its own group of 6 sheep subjects, and the plasma growth hormone levels of the sheep monitored every few days over a 21 day cycle. On the day prior to bleeding, the sheep were fasted approximately 16 hours prior to the blood sample. The animals were allowed to feed freely for 30 minutes prior to drawing the blood samples at each sampling. ANOV and mean separation procedures were applied to the plasma data. The results of this testing are set forth in FIGS. 3-6, which are graphs of plasma growth hormone levels over time for the sheep subjects. The data points for each formulation were derived from the statistical analysis of the 6 subjects treated with that formulation.

As can be seen in the Figures, all treatments provided sustained release of GRF for at least 14 days as evidenced by elevated growth hormone levels over this period. As can also be seen, dextran can be included in formulations to increase the amount of drug delivered and the duration of release.

EXAMPLE 23

Synthesis of p-Methyl Hippuroyl pGRF (2-76)OH

The following procedures were used to synthesize p-Methyl Hippuroyl porcine GRF ("pGRF") (2-76-)OH having the formula (SEQ ID. NO. 1):

THR—GLN—LEU—SER—ALA—ARG—ARG—LEU—LEU—GLN—ASP—ILE—LEU—SER—ARG—
15                    20                              25

GLN—GLN—GLY—GLU—ARG—ASN—GLN—GLU—GLN—GLY—ALA—ARG—VAL—ARG—LEU—
30                         35                             40

GLY—ARG—GLN—VAL—ASP—SER—LEU—TRP—ALA—ASP—GLN—ARG—GLN—LEU—ALA—
45                         50                             55

LEU—GLU—SER—ILE—LEU—ALA—THR—LEU—LEU—GLN—GLU—HIS—ARG—ASN—SER—
60                       65                              70

GLN—GLY—OH

23.A. Rcombinant Expression of pGRF (2-76)OH
23.A.1. Synthesis of Plasmid pHS452 Encoding Met$_1$-pGRF (2-76)OH Plasmid pHS452 is a recombinant DNA expression vector which produces large amounts of pGRF (2-76-)OH polypeptide when the host cell is cultured under the proper conditions.

A lyophil of *E. coli* K12 RV308/pHS190 can be obtained from the Northern Regional Research Laboratories (NRRL), Peoria, Ill. 61604, under the accession number NRRL B-18410 (date of deposit: Sep. 9, 1988) and used directly as the "culture" in the process below. Ten milliliters of TY broth (10 g trypton, 5 g NaCl, and 5 g yeast extract per liter) containing 5 mg/ml of tetracycline is innoculated with a culture of *E. coli* K12 RV308/pHS190 and incubated with aeration at 30° C. overnight (15-18 hours). The resulting culture is used as a source of plasmid pHS190.

One liter of TY broth containing 5 mg/ml tetracycline is innoculated with a culture of *E. coli* K12 RV308/pHS190 and incubated with aeration at 32° C. overnight (15-18 hours). The culture is then centrifuged at 5200 rpm in a Sorvall (DuPont Co., Instrument Products, Biomedical Division, Newtown, Conn. 06470) GSA rotor for 10 minutes at 4° C. to pellet the cells. The resulting supernatant is discarded. The cell pellet is resuspended in 28 ml of a solution of 25% sucrose and 50 mM EDTA (ethylenediamine tetracetic acid). About 1 ml of a solution of 20 mg/ml lysozyme in 0.25M tris-HCl (tris(hydroxymethyl)aminomethane hydrochloride), pH=8.0, and about 1.5 ml of 0.5M EDTA, pH=8.0, are added to and mixed with the cell suspension. The resulting mixture is incubated on ice for 15 minutes. Three milliliters of lysing solution (prepared by mixing 3 ml of 10% Triton ® X-100 (Rohm & Haas); 75 ml of 0.25M EDTA, pH=8.0 and 7 ml of water) are added to the lysozyme-treated cells with gentle mixing. The resulting solution is incubated on ice for another 15 minutes.

The cellular debris is removed from the solution by centrifugation at 17,000 rpm in a Sorvall SS34 rotor for about 45 minutes at 4° C. About 28.6 g of CsCl and ~1 ml for a 5 mg/ml ethidium bromide solution are added to the ~30 ml of supernatant. Then, the volume is adjusted to 40 ml with water and the solution decanted into an ultracentrifuge tube. Th tube is sealed, and the solution is centrifuged at 49,500 rpm in a Ti70 rotor (Beckman, 7360 N. Lincoln Avenue, Lincolnwood, Ill. 60646) for ~18 hours. The resulting plasmid band, visualized with ultraviolet light, is isolated, extracted with CsCl-saturated isopropanol to remove the ethidium bromide, and dialysed against three changes of ~20 volumes of TE buffer (10 mM Tris-HCl, pH=7.5, and 1 mM EDTA). The dialysate is collected; then, two volumes of ethanol and 0.05 volumes of 3M sodium acetate solution are added. The ethanol mixture is cooled to −20° C., and the plasmid DNA is pelleted by centrifugation at 10,000 rpm for 30 minutes in an SS34 rotor at −10° C. The resulting pellet is resuspended in ~1 ml of TE buffer and then extracted with an equal volume of a phenol:chloroform mixture (1:1, v/v). The DNA in the aqueous phase is recovered by the addition of 0.1 volume of 3M sodium acetate and 2 volumes of ethanol, followed by incubation at −20° C. for ~30 minutes and centrifugation at 15,000 rpm in an SS34 rotor for 20 minutes. The resulting DNA pellet is rinsed first with 70% ethanol and then with 100% ethanol and dried.

The ~1.0 mg of plasmid pHS190 DNA obtained by the above procedure is suspended in 1.5ml of 0.1X TE buffer and stored at −20° C. About 10 mg of plasmid pHS190 DNA are digested with restriction enzyme EcoRI (~10 units) in a reaction containing the DNA in EcoRI buffer (100 mM Tris-HCl pH=7.5, 5 mM MgCl, 50 mM NaCl). The reaction is incubated for 2 hours at 37° C.

To convert the 5' overhanging ends to blunt ends 0.5 mM of each dNTP (dATP, dCTP, dGTP, and TTP) is added along with 1-5 units Klenow fragment (Boehringer Mannhelm Biochemicals, 7941 Castleway Dr., P.O. Box 50816, Indianapolis, Ind. 46250). The reaction mixture is extracted with phenol, phenol/chloroform, chloroform and then ethanol precipitated.

The plasmid is then resuspended in 50 ml of a solution containing 40 mM Tris HCL, pH 7.5, 10 mM MgCl, 10 mM dithiothreitol (DTT), 0.5 mM adenosine triphosphate, and 1 U T4 DNA ligase (Boehringer-Mannheim Biochemicals, 7941 Castleway Drive, Indianapolis, Ind. 46250). The reaction is incubated at 14° C. overnight.

The ligated mixture was transformed into *E. coli* K12 RV308 (available from the NRRL as NRRL B-15624) by the following procedure from Maniatis et al., Molecular Cloning, pg. 250-251 (Cold Spring Harbor Press, 1982). One hundred milliliters of TY broth in a 500-ml flask was innoculated with 1 ml of an overnight culture of RV308. The cells were grown with vigorous shaking at 37° C. to a density of ~5×10⁷ cells/ml. The culture was placed on ice for ten minutes, then centrifuged at 4000× g for 5 minutes at 4° C. The cells were resuspended in 50 ml ice-cold 50 mM CaCl in 10 mM Tris-HCl, pH=8.0. The cells were again incubated on ice for 15 minutes and recentrifuged. The cells were then resuspended in 3.3 ml of the calcium chloride solution. The ligation mixture was added to 200 ml of cells and incubated on ice for 30 minutes. The cells were then transferred to a 42° C. water bath for 2 minutes. One ml of TY broth was added to the tube and the cells were incubated for one hour at 30° C. Two hundred microliter aliquots were then plated onto TY agar (TY broth+1.5% agar) plates containing 5 mg/ml tetracycline and grown overnight at 30° C.

The plasmid is then resuspended in 10 ml of water. The vector is generated by digesting the plasmid with XbaI and BamHI. About 1 ml of XbaI (~10 units) is added to 10 ml plasmid DNA (~10 mg) and 5 ml 10× XbaI buffer (500 mM Tris-HCl, pH=8.0, 100 mM MgCl, and 500 mM NaCl). After incubation at 37° C. for 90 minutes, 0.5 ml of 5M NaCl and 1 ml BamHI (10 units) are added and the incubation continued at 37° C. for an additional 90 minutes. The reaction mixture is then subjected to agarose gel electrophoresis, and the ~5.75 kb XbaI-BamHI vector fragment is isolated by electroelution followed by ethanol precipitation.

The following DNA sequence (Seq. I.D. No. 2) was synthesized on an Applied Biosystems Model 380B synthesizer using techniques well-known to one skilled in the art. The process by which construction of the synthetic gene is achieved by division of the sequence into oligonucleotides and subsequent ligation of these oligonucleotids was achieved in substantial accordance with the procedure of Brown, et al., Methods in Enzymology 68:109 (1979):

```
ATG GCT GAT GCT ATT TTT ACT AAT AAT TAT CGA CGC GTT

CTT ACT CAG CTG TCT GCT CGT CGT CTG CTG CAG GAT ATT

CTG TCT CGT CAG CAG GGT GAA CGT AAC CAG GAA CAA GGA

GCT CGT GTT CGT CTT GGT CGT CAG GTT GAT TCT CTG TGG

GCT GAT CAA CGT CAG CTT GCT CTC GAG TCT ATC CTG GCT

ACT CTG CTG CAG GAA CAT CGT AAT TCT CAG GGT TAA TAG
```

The DNA comprising the coding sequence was then mixed with and ligated to the XbaI-BamHI vector fragment constructed above. The ligated mixture was then transformed in E. coli K12 RV308 as described above. The plasmid DNA of tretracycline-resistant transformants was analyzed by restriction enzyme digestion to verify that the plasmid was pHS452.

23.B. Isolation of Recombinant pGRF Peptide

23.B.1. Expression of the pGRF Analog in E. coli

E. coli K12 RV308/pHS452 was grown in TY broth containing 5 mg/ml tetracycline at 32° C. until the cells reached mid-log phase. The temperature of the mixture was raised to 42° C. and incubation continued for about 3 more hours. The cI857 temperature-sensitive repressor of the lambda pL promoter, positioned to drive GRF analog expression on plasmid pHS452, is inactivated at 42° C., thus allowing the expression of the GRF analog.

23.B2. Isolation of Granules Containing the GRF Analog

When using a high level E. coli expression system as exemplified herein, the protein product is sequestered in inclusion bodies or granules. The granules containing the GRF analog are isolated and solubilized to isolate the GRF peptide of interest. First, the whole cells are centrifuged, then resuspended in water at 10° C. The cell slurry is homogenized in a Gaulin homogenizer at 8000 psig. The homogenized slurry is then diluted in water and agitated for 10 minutes, followed by adjustment of the pH to 8.4–8.6 with 10% sodium hydroxide. The mixture is then centrifuged. The solids represent the GRF analog-containing granules, which are frozen at −70° C. until further use.

23.B.3. Final Purification of th GRF Analog

The granules prepared in Example 23.B.2. above are thawed at 2°–5° C. The granules are solubilized by the addition of ten volumes of 0.05N acetic acid-7M urea followed by homogenization for 5–8 minutes. The pH is then adjusted to 2.5–2.6 by the addition of 10%-hydrochloric acid. The mixture is agitated 12–15 hours at 2°–5° C. The solution is clarified by filtration through a Sparkler filter coated with Dicalite Speedex filter aid (Grefco, Torrance, Calif.). The conductivity of the solution is reduced to less than 4000 mohms by dilution with the acetic acid-urea solution.

A cation exchange column is prepared using S Sepharose ® (Pharmacia, 800 Centennial Ave., Piscataway, N.J. 08854) resin. The column contains one liter of resin per 50 g of material. The material is added to the column at a flow rate of 0.1 l/cm/hr and washed with 2 column volumes of 0.1M sodium chloride in the acetic acid-urea solution. The GRF analog is eluted by a linear gradient of 0.25M to 1.6M sodium chloride in acetic acid-urea using three column volumes of each with 0.1 column volume fractions collected. The GRF analog-containing fractions are identified by conductivity, $O.D._{276}$, HPLC and polyacrylamide gel electrophoresis. The fractions are then pooled.

An equal volume of acetic acid-urea solution is added to the pooled fractions. The material is then applied to a column containing S Sepharose ® resin in acetic acid-urea sized to accommodate 50 g of protein per liter of resin. The flow rate is 0.02 l/cm²/hr. The GRF analog fractions are eluted by a linear gradient of 0.25M to 1.2M sodium chloride in acetic acid-urea. Fractions of 0.1 column volume are collected. The fractions are analyzed as before and the GRF analog-containing fractions are pooled.

A Sephadex ® G-15 (Pharmacia) column is prepared in 0.02M glycine, pH 2.5 with a column volume five times the volume of the previously pooled fractions. Fractions containing the $O.D._{276}$ peak are isolated.

A column containing SP20Ss resin (Sephabeads ®, Mitsubishi Chemical, Tokyo) in 10% acetonitrile-0.02M glycine, pH 2.5, is then prepared. The pooled GRF analog-containing solution is made 10% in acetonitrile and added to the column at a flow rate of 1.5-2 column volumes per hour. The column is washed with 2 column volumes of the acetonitrile-glycine buffer. The GRF analog is eluted by a gradient formed by three column volumes of 10% acetonitrile-0.02M glycine mixed with three column volumes 50% acetonitrile-0.02M glycine. Fractions of 0.1 column volume are collected and assayed for the GRF analog.

The GRF analog-containing material is then chromatographed over a Sephadex® G15 column equilibrated in 0.25M acetic acid. The $O.D._{276}$ peak is then isolated and lyophilized until further use.

23.C. Preparation of p-Methyl Hippuroyl pGRF(2-76)OH.

23.C.1. Synthesis of p-methylbenzoyl glycine.

Approximately 7.5 g of glycine was dissolved in a solution comprised of 105 ml of 2N NaOH and 50 ml of dioxane with mechanical stirring at 0°-5° C. Approximately 14.9 ml of p-toluoyl chloride was diluted to a volume of 50 ml with dioxane and added dropwise to the reaction over a period of 15 to 20 minutes. The reaction mixture was stirred overnight with warming to 25° C. (i.e. room temperature).

The reaction was basified with aqueous NaOH and extracted with diethyl ether. The aqueous phase was acidified to pH3.0 with 6N HCl. The aqueous phase was extracted with EtOAc. The EtoAc was washed with $H_2O$ and dried over $MgSO_4$, filtered, and the filtrate concentrated in vacuo to near dryness. The solids were suspended in $Et_2$, O filtered and dried in vacuo to produce 14.25 g of what was later demonstrated to be p-methyl hippuric acid. The identity of the product was confirmed by melting point and elemental combustion analysis which compared favorably with the theoretical values for p-methyl hippuric acid. The melting point of the compound produced above was 151°-154° C.

23.C.2. Synthesis of p-methyl hippuroyl pGRF(2-76) OH

Approximately 1.65 g of pLmethylhippuric acid, prepared in substantial accordance with the teachings of Example 23.C.1. above, was dissolved in 15 ml of dimethylformamide (DMF) with stirring and cooling in an ice bath. Approximately 1 g of N-hydroxy succinimide was added to the solution followed by 1.9 g of DCC. The reaction was stirred overnight with warming to room temperature (25° C.).

The DCU precipitate was isolated by filtration and the filtrate was concentrated in vacuo. The residual oil was diluted with $Et_2O$ and some crystallization occurred. The solids were isolated by filtration, washed with $Et_2O$, and dried in vacuo to yield 3.28 g of product having a melting point of 167°-170° C. The material was subjected to elemental combustion analysis the results of which compared well with the theoretical values expected for the succinimidyl ester of p-methyl hippuric acid ($C_{14}H_{14}N_2O_5$).

Approximately 72 mg of pGRF(2-76)OH prepared in substantial accordance with the teaching of Example 23.A. above, was dissolved in 3 ml of 0.1M Tris-HCl, pH7.8, 30% propanol with stirring at room temperature. To the reaction 57 mg of the succinimidyl ester of p-methyl hippuric acid was added and the reaction stirred at room temperature while removing 5 µl samples at 15 min., 1 hour, and 2 hours after introduction of the succinimidyl N-(p-methyl) hippuric acid to follow the progress of the reaction. Each of these samples was diluted to 500 ml with 0.1% TFA and injected onto a 0.46×15 cm Vydac C18 column for RP-HPLC analysis and comparison with the starting material.

After 2.5 hours the reaction mixture was acidified with approximately 1 ml of glacial HOAc and applied to a 2.2×28.5 cm Sephadex G-10 column. The column was eluted with 10% HOAc and 7.5 ml fractions were collected. The $ABS_{280}$ of each fraction was determined to indicate the presence of polypeptidyl compounds. Fractions 7 through 10 indicating the presence of polypeptide were combined, frozen, and lyophilized to give 70 mg of lyophilisate.

While the invention has been described in detail, the same is to be considered as illustrative and not restrictive in character, it being understood that only the preferred embodiment has been described and that all changes and modifications that come within the spirit of the invention are desired to be protected.

What is claimed is:

1. A composition of matter of an injectable extended release formulation comprising a growth hormone-related substance selected from the group consisting of growth hormones and growth hormone releasing factors in a carrier including a biocompatible hydrophobic vehicle and an effective amount of polyglycerol ester to extend release of the substance in an animal.

2. The composition of claim 1 wherein the polyglycerol ester is completely esterified.

3. The composition of claim 1 wherein the growth hormone-related substance is a growth hormone.

4. The composition of claim 1 wherein the growth hormone-related substance is a growth hormone releasing factor.

5. The composition of claim 1 wherein the growth hormone-related substance is in simple admixture with the carrier.

6. The composition of claim 1 wherein the carrier also includes an amount of dextran effective to further extend said release.

7. The composition of claim 1 wherein the polyglycerol ester is a semi-solid.

8. The composition of claim 3 wherein the growth hormone is bovine growth hormone.

9. The composition of claim 4 wherein the growth hormone releasing factor is p-methyl hippuroyl pGRF(2-76)OH.

10. The composition of claim 7 wherein the biocompatible hydrophobic vehicle is an oil.

11. The composition of claim 8 wherein the bovine growth hormone is somidobove.

12. The composition of claim 10 wherein the weight ratio of polyglycerol ester to oil is about 10:90 to about 60:40.

13. The composition of claim 12 wherein the growth hormone-related substance is bovine growth hormone.

14. The composition of claim 12 wherein the growth hormone-related substance is growth hormone releasing factor.

15. The composition of claim 12 wherein the ester in the polyglycerol ester is selected from the group consisting of laurate, myristate, palmitate, stearate, arachidate, behenate, lignocerate, palmitoleate, oleate, linoleate, linolenate, and arachidonate.

16. The composition of claim 13 wherein the bovine growth hormone is somidobove.

17. The composition of claim 14 wherein the growth hormone releasing factor is p-methyl hippuroyl pGRF(2-76)OH.

18. The composition of claim 15 wherein the ester in the polyglycerol ester is oleate.

19. The composition of claim 15 wherein the ester in the polyglycerol ester is stearate.

20. The composition of claim 19 wherein said polyglycerol ester is diglycerol tetrastearate.

21. A method for making a composition for treating an animal with a growth hormone-related substance selected from the group consisting of growth hormones and growth hormone releasing factors, comprising incorporating the growth hormone-related substance in a carrier including polyglycerol ester and a biocompatible hydrophobic vehicle to thereby form an injectable formulation, said polyglycerol ester being included in an amount effective to extend release of the growth hormone-related substance in an animal.

22. The method of claim 21 in which the polyglycerol ester is a semi-solid.

23. The method of claim 21 wherein the polyglycerol ester is completely esterified.

24. The method of claim 21 wherein growth hormone is incorporated in the carrier.

25. The method of claim 21 wherein growth hormone releasing factor is incorporated in the carrier.

26. The method of claim 24 wherein the growth hormone is bovine growth hormone.

27. The method of claim 25 wherein the growth hormone releasing factor is p-methyl hippuroyl pGRF(2-76)OH.

28. The method of claim 26 wherein the bovine growth hormone is somidobove.

29. The method of claim 21 wherein the carrier also includes an amount of dextran effective to further extend said release.

30. The method of claim 21 wherein the hydrophobic biocompatible vehicle is an oil.

31. The method of claim 30 wherein the weight ratio of polyglycerol ester to oil is about 10:90 to about 60:40.

32. The method of claim 31 wherein bovine growth hormone is incorporated in the carrier.

33. The method of claim 31 wherein growth hormone releasing factor is incorporated in the carrier.

34. The method of claim 32 wherein the bovine growth hormone is somidobove.

35. The method of claim 33 wherein the growth hormone releasing factor is p-methyl hippuroyl pGRF(2-76)OH.

36. The method of claim 31 wherein the ester in the polyglycerol ester is selected from the group consisting of laurate, myristate, palmitate, stearate, arachidate, behenate, lignocerate, palmitoleate, oleake, linoleate, linolenate, and arachidonate.

37. The method of claim 36 wherein the ester in the polyglycerol ester is oleate.

38. The method of claim 36 wherein the ester in the polyglycerol ester is stearate.

39. The method of claim 38 wherein said polyglycerol ester is diglycerol tetrastearate.

40. A method for administering a growth hormone-related substance selected from the group consisting of growth hormones and growth hormone releasing factors to an animal, comprising injecting into said animal an injectable, extended release formulation including the growth hormone-related substance in a carrier including a biocompatible hydrophobic vehicle and an amount of polyglycerol ester effective to extend release of the substance in the animal.

41. The method of claim 40 wherein the polyglycerol ester is completely esterified.

42. The method of claim 40 wherein the substance is a growth hormone.

43. The method of claim 40 wherein the substance is a growth hormone releasing factor.

44. The method of claim 41 wherein the substance is a growth hormone.

45. The method of claim 42 wherein the growth hormone is bovine growth hormone.

46. The method of claim 43 wherein the growth hormone releasing factor is p-methyl hippuroyl pGRF(2-76)OH.

47. The method of claim 45 wherein the bovine growth hormone is somidobove.

48. The method of claim 40 wherein the carrier also includes an amount of dextran effective to further extend said release.

49. The method of claim 40 wherein the polyglycerol ester is a semi-solid.

50. The method of claim 49 wherein the biocompatible hydrophobic vehicle is an oil.

51. The method of claim 50 wherein the weight ratio of polyglycerol ester to oil is about 10:90 to about 60:40.

52. The method of claim 51 wherein the substance is a growth hormone.

53. The method of claim 51 wherein the substance is a growth hormone releasing factor.

54. The method of claim 52 wherein the growth hormone is bovine growth hormone.

55. The method of claim 53 wherein the growth hormone releasing factor is p-methyl hippuroyl pGRF(2-76)OH.

56. The method of claim 54 wherein the bovine growth hormone is somidobove.

57. The method of claim 51 wherein the ester in the glycerol or polyglycerol ester is selected from the group consisting of laurate, myristate, palmitate, stearate, arachidate, behenate, lignocerate, palmitoleate, oleate, linoleate, linolenate and arachidonate.

58. The method of claim 57 wherein the ester in the polyglycerol ester is oleate.

59. The method of claim 57 wherein the ester in the polyglycerol ester is stearate.

60. The method of claim 59 wherein said polyglycerol ester is diglycerol tetrastearate.

* * * * *